United States Patent [19]

Renner et al.

[11] Patent Number: 4,855,441

[45] Date of Patent: Aug. 8, 1989

[54] PROCESS FOR THE PREPARATION OF THIOETHER COMPOUNDS

[75] Inventors: Günter Renner, Bergisch Gladbach; Erich Illner, Leichlingen, both of Fed. Rep. of Germany

[73] Assignee: Agfa-Gevaert Aktiengesellschaft, Leverkusen, Fed. Rep. of Germany

[21] Appl. No.: 132,595

[22] Filed: Dec. 14, 1987

[30] Foreign Application Priority Data

Dec. 24, 1986 [DE] Fed. Rep. of Germany ....... 3644406

[51] Int. Cl.$^4$ ................. C07D 231/00; C07D 263/04; C07D 277/04; C07D 403/00
[52] U.S. Cl. .................................... 548/363; 548/365; 548/225; 548/182; 548/336; 548/144; 548/136; 548/251; 548/374; 548/364; 548/221
[58] Field of Search ............... 548/363, 364, 365, 225, 548/182, 336, 374, 144, 136, 251, 374, 221

[56] References Cited

U.S. PATENT DOCUMENTS 3,485,632  12/1969  Ohlschlager ........................ 548/365

Primary Examiner—Mary C. Lee
Assistant Examiner—Robert C. Whittenbaugh
Attorney, Agent, or Firm—Connolly & Hutz

[57] ABSTRACT

5-pyrazolone compounds which are substituted with a thioether group in the 4-position may be prepared by the reaction of a 5-pyrazolone compound which is unsubstituted in the 4-position with a sulphenic acid amide. The resulting 5-pyrazolone compounds substituted in the 4-position are suitable for use as 2-equivalent magenta couplers in colour photographic recording materials.

6 Claims, No Drawings

PROCESS FOR THE PREPARATION OF THIOETHER COMPOUNDS

This invention relates to a process for the preparation of thioether compounds of the formula Py—S—R wherein Py denotes the residue of a pyrazolone magenta coupler and R denotes alkyl, cycloalkyl, aralkyl, aryl or a heterocyclic group by the reaction of a pyrazolone magenta coupler which is unsubstituted in the 4-position with a suitable sulphenic acid amide compound.

Compounds of the formula Py—S—R have been known for a long time. In the field of colour photography, for example, they are suitable for use as so-called 2-equivalent magenta couplers. These are couplers which give rise to a magenta dye on chromogenic development in the presence of exposed silver halide but with the consumption of only 2 oxidation equivalents instead of the 4 oxidation equivalents required when the corresponding 4-equivalent couplers are used. The said 4-equivalent couplers are unsubstituted in the coupling position, in contrast to the 2-equivalent couplers which carry in their coupling position a substituent which is released in the process of chromogenic development. The use of 2-equivalent couplers is advantageous because it requires a smaller quantity of exposed silver halide for producing a given quantity of dye or obtaining a given colour density in a colour photographic recording material than the use of the corresponding 4-equivalent coupler. This advantage is reflected both in the production cost of the colour photographic recording material and in the resolution and sharpness of the colour image produced. 2-equivalent magenta couplers are in many cases further distinguished from the corresponding 4-equivalent magenta couplers by their higher reactivity, which has the advantage of reducing the development time. If the residue S—R is capable of inhibiting silver halide development after it has been released from the coupling position then the coupler is a so-called DIR coupler. Compounds of the formula Py—S—R have been described, for example, in U.S. Pat. No. 3,227,554, GB-A-1 379 398, DE-A-29 44 601 and U.S. Pat. No. 4,556,630.

The following are examples of processes known for the preparation of compounds of the formula Py—S—R:

The reaction of a pyrazolone which is unsubstituted in the 4-position with a sulphenyl chloride of the formula Cl—S—R as described, for example, in U.S. Pat. No. 3,227,554;

The reaction of a pyrazolone which is unsubstituted in the 4-position with a mercaptan of the formula H—S—R under the action of bromine as described, for example, in Research Disclosure 13 806 (October, 1975);

The reaction of a pyrazolone which is unsubstituted in the 4-position with a S-alkyl-isothiourea as described, for example, in DE-A-29 44 601;

The reaction of a pyrazolone which is halogenated in the 4-position with a mercaptan;

The reaction of a pyrazolone which is unsubstituted in the 4-position with a thiosulphonic acid ester as described, for example, in DE-A-32 41 886.

The present invention relates to a new process for the preparation of compounds of the formula Py—S—R. The processes described in U.S. Pat. No. 3,227,554 and Research Disclosure 13806 are subject to limitations in the nature of the mercaptan used in that although they are suitable for heterocyclic mercaptans and aryl mercaptans, they are not suitable for alkyl mercaptans because these form numerous side products. The said processes are therefore not universally applicable. Furthermore, the sulphenyl chloride used is in many cases so unstable that only low yields can be obtained. The process described in DE-A 29 44 601 also is not universally applicable and is less suitable, for example, for the introduction of arylthio residues and heterocyclic thio residues. Moreover, many salts of S-alkylthio-isothioureas which may be used in this process are difficult to purify.

The process described in DE-A-32 41 886 gives satisfactory results but is expensive because sulphinic acid salts which are expensive starting materials are required for the preparation of the necessary thiosulphonic acid esters.

It is an object of the present invention to provide a new and advantageous process for the preparation of pyrazolones which are substituted with a thioether group in the 4-position.

The present invention relates to a process for the preparation of thioether compounds of the formula Py—S—R (I), wherein:

Py denotes the residue of a 5-pyrazolone compound to which the group S—R is attached in the 4-position and R denotes an alkyl, alkenyl, cycloalkyl, aralkyl, aryl or heterocyclic group by the reaction of a compound of the formula Py*—H, wherein Py* denotes the residue of a 5-pyrazolone compound which is unsubstituted in the 4-position and from which a hydrogen atom has been removed in the 4-position with a reactant for introducing a thioether group into the 4-position of the 5-pyrazolone compound, characterized in that the compound of the formula Py*—H is reacted with a compound of the formula B—S—R (II) wherein R has the meaning already indicated and
B stands for

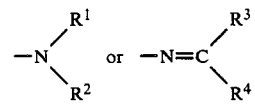

wherein
$R^1$ denotes alkyl, aralkyl or aryl
$R^2$ denotes alkyl, aralkyl or $SO_2$—$R^5$ or $R^1$ and $R^2$ together stand for the group required to complete a 5-membered or 6-membered heterocyclic ring,
$R^3$ and $R^4$ denote dialkylamino and
$R^5$ denotes alkyl, aryl or dialkylamino.

The residue of a 5-pyrazolone compound denoted by Py or Py* may be in particular a residue corresponding to the formula

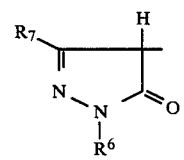

wherein $R^6$ denotes an aryl group, in particular a phenyl group optionally carrying one or more substituents or it may denote alkyl, aralkyl or a heterocyclic group, and $R^7$ may denote an amino or acylamino residue but may also stand for alkyl, aryl, alkoxy, aryloxy, carboxy, cyano, carbamoyl or a carboxylic acid ester group.

An amino group denoted by $R^7$ may be an alkyl-substituted or aryl-substituted amino group, or it may be a cyclic amino group, for example a pyrrolidinone, piperidine or morpholine group. An acyl amino group denoted by $R^7$ is one in which the acyl group may be derived from an aliphatic or aromatic carboxylic acid or from a carbamic acid or from a carbonic acid monoester.

An alkyl group denoted by R in formula I may be straight chained or branched, may be substituted and may contain up to 20 carbon atoms. The following are examples: methyl, ethyl, propyl, i-propyl, butyl, t-butyl, hexyl, octyl, decyl, dodecyl, hexadecyl, and octadecyl.

An alkenyl group denoted by R in formula I may be, for example, an allyl group; a cycloalkyl group may be, for example, cyclohexyl;

an aralkyl group may be, for example, benzyl or phenylethyl;

an aryl group may be, for example, phenyl or naphthyl;

a heterocyclic group is in particular a group corresponding to the formula wherein Q denotes the group required for completing a 5-membered or 6-membered heterocyclic ring which may carry additional, condensed carbocyclic or heterocyclic rings. All these groups (cycloalkyl, aralkyl, aryl, heterocyclic groups) may in turn be substituted.

A group denoted by Q in the above formula may be, for example, a group which completes a pyrrole, oxazole, thiazole, imidazole, pyrazole, oxadiazole, thiadiazole, triazole, or tetrazole ring.

An aryl group denoted by R may be, in particular, a phenyl group which may be mono substituted, di-substituted or trisubstituted, e.g. by halogen (in particular chlorine) or by alkyl, aralkyl, alkoxy, alkylthio, aryloxy, amino, acylamino or nitro.

In the process according to the invention, a suitable sulphenic acid amide corresponding to the formula B—S—R (II) is used for the introduction of a thioether group into the 4-position of the pyrazolone compounds. In this formula (II) B (amine component) may be, for example, groups (B-) corresponding to the following formulae:

-continued

B-14 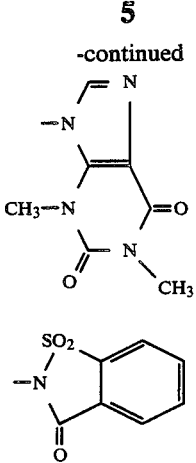

B-15 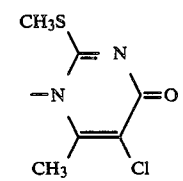

B-16 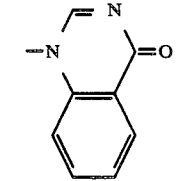

B-17 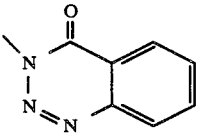

B-18 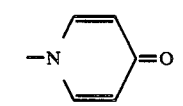

B-19 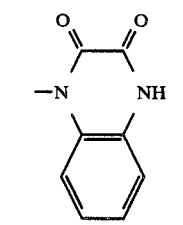

B-20 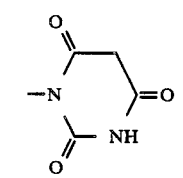

B-21 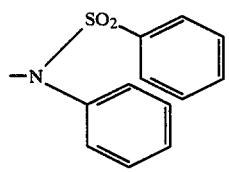

B-22 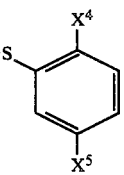

-continued

B-23 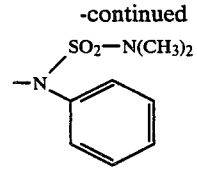

B-24 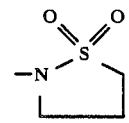

In formula II the group -S—R (mercaptan component) may, for example, stand for one of the following groups:

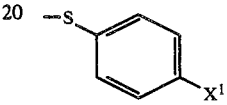

$X^1 = H$
$= -CH_3$
$= Cl$
$= -\underset{\underset{CH_3}{|}}{\overset{\overset{CH_3}{|}}{C}}-CH_3$
$= -C_{12}H_{25}$
$= -NH-CO-C_9H_{19}$
$= -NO_2$ $X^2 = X^3 = -CH_3$
$= -CH(CH_3)_2$
$= -C(CH_3)_3$
$= Cl$
$= -O-C_4H_9$
$= -\underset{\underset{CH_3}{|}}{\overset{\overset{CH_3}{|}}{C}}-CH_2-CH_3$ $X^2 = -O-C_4H_9 \qquad X^3 = -C_2H_5$ $X^4 = X^5 = -C(CH_3)_3$
$= -CH(CH_3)_2$
$= Cl$
$= -CH_2-\phi$
$= -OC_4H_9$

| $X^4 =$ | $-S-CH_3$ | $X^5 =$ | $-CH_3$ |
| | " | | $-C(CH_3)_3$ |
| | " | | $-C(CH_3)_2-CH_2-C(CH_3)_3$ |
| | $-S-C_4H_9$ | | $-C(CH_3)_3$ |
| | | | $-C(CH_3)_2-CH_2-C(CH_3)_3$ |
| | $-O-CH_3$ | | $-C(CH_3)_3$ |
| | | | $-C(CH_3)_2-CH_2-C(CH_3)_3$ |
| | $-O-C_4H_9$ | | " |
| | | | $-C(CH_3)_3$ |

-continued

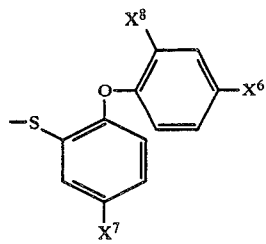

| $X^7$ | $X^8$ | $X^6$ |
|---|---|---|
| $= -C(CH_3)_3$ | $= H$ | $= -N(C_4H_9)_2$ |
| $= -C_8H_{17}-t$ | $= H$ | $= -N(C_2H_5)_2$ |
| $= -C_8H_{17}-t$ | $= H$ | $= -SO_2-C_2H_5$ |
| $= -C_4H_9-t$ | $= -N(C_4H_9)_2$ | $= -N(C_4H_9)_2$ |
| $= -C_4H_9-t$ | $= -N(C_4H_9)_2$ | $= -CF_3$ |

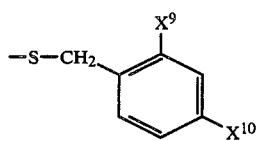

| $X^9$ | $X^{10}$ |
|---|---|
| $= H$ | $= -C_{12}H_{25}$ |
| $= Cl$ | $= Cl$ |
| $= -OC_4H_9$ | $= -C_6H_{13}-t$ |
| $= -OCH_3$ | $= -OCH_3$ |
| $= -S-C_{12}H_{25}$ | $= -S-CH_2-CH=CH_2$ |
| $= -S-C_{16}H_{33}$ | $= -S-CH_2-COOH$ |

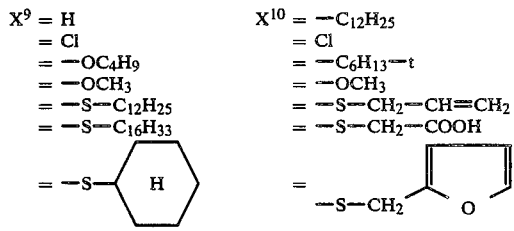

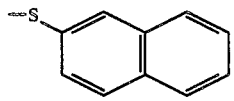

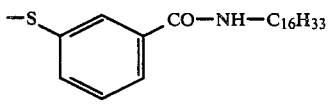

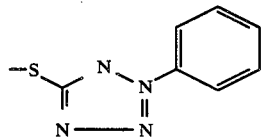

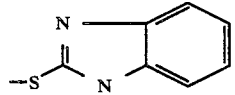

Sulphenic acid amides (formula II) may be obtained by various methods but two main methods should be distinguished:
1. Starting from a sulphenic acid halide (R—S Hal), a reaction with a secondary amine (H—B) is carried out under basic catalysis in a non-protic solvent (e.g. acetonitrile, DMF, dimethylacetamide, sulpholan, methylenechloride). The sulphenic acid halide used may be formed in situ by the reaction of disulphanes with halogen.
2. Starting from N-halogen compounds (Hal-B), the aliphatic or aromatic thiol (R—S—H) is directly converted into the end product under conditions similar to those indicated above.

Several methods are available for the preparation of sulphenic acid halides (method 1). Among these the reaction of thiols (R—S—H) with a halogenating agent such as sulphuryl chloride, chlorosuccinimide, sodium hypochlorite, bromine or chlorine has been found advantageous but disulphanes and to some extent sulphanes may be used instead of thiols for the preparation of the sulphenic acid halides.

The sulphenic acid amides mentioned above may also be isolated solvent free, in which case the compounds obtained are in some cases well crystallized and therefore readily purified. It is preferred, however, to employ a process in which the sulphenic acid amides obtained are not isolated and the organic solution of the sulphenic acid amides, which are frequently obtained in almost quantatative yield, are used directly for the synthesis of compounds of formula I.

The sulphenic acid amides used for the synthesis and the appropriate 5-pyrazolone compounds which are unsubstituted in the 4-position may be reacted together in any of a wide variety of solvents, such as ethyl acetate, acetonitrile, tetrahydrofuran, acetone, methylene chloride, toluene, dimethylsulphoxide or dimethylacetamide. The sulphenic acid amide is put into this reaction in an equimolar quantity or in an excess of up to 100%, preferably up to 40%, based on the pyrazolone compound. The reaction is suitably carried out at room temperature or with slight heating, up to 80° C.

The synthesis of mercapto compounds and thiols (R—S—H) is known and has been described in the relevant literature. Many of the compounds R—S—H mentioned are also available commercially.

The following are examples of compounds of the formula Py*—H which may be converted into the corresponding thioether compounds of formula I by the reaction with sulphenic acid amides by the process according to the invention:

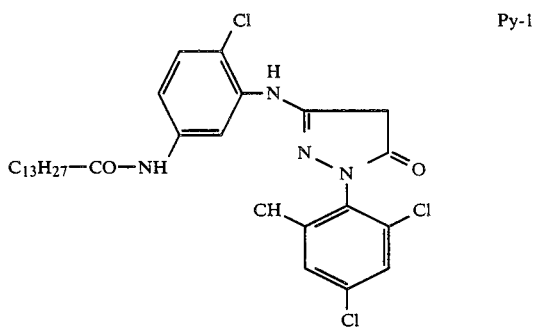

Py-1

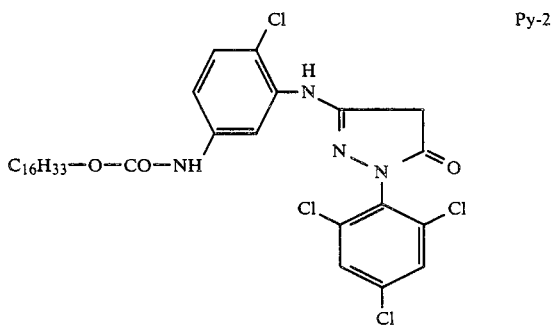

Py-2

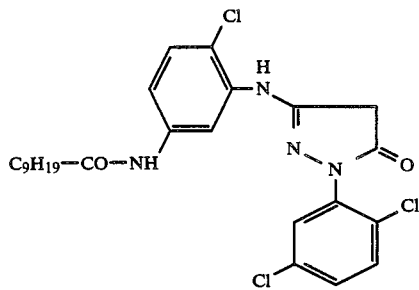

Py-3

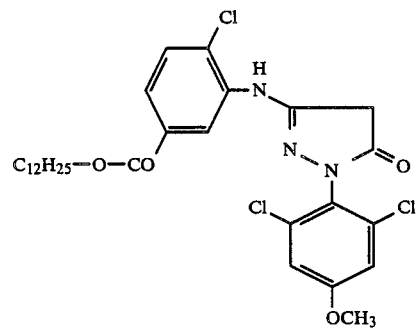

Py-4

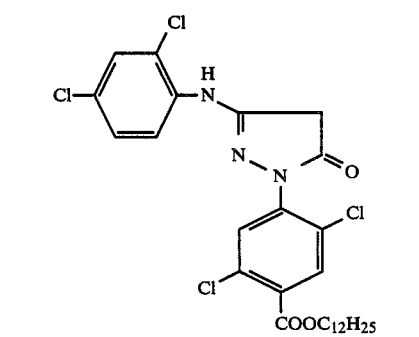

Py-5

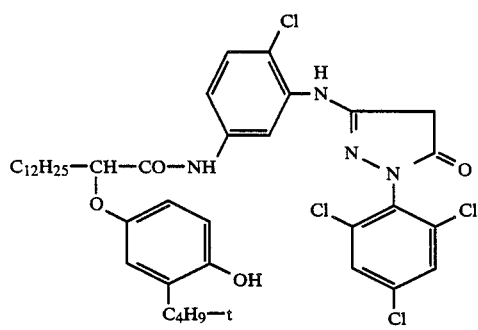

Py-6

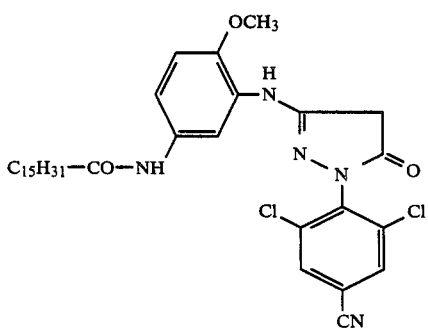

Py-7

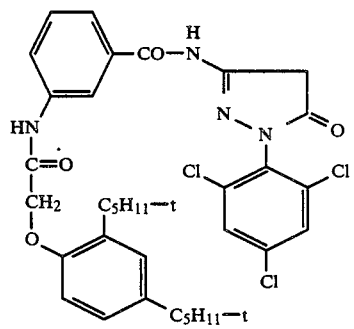

Py-8

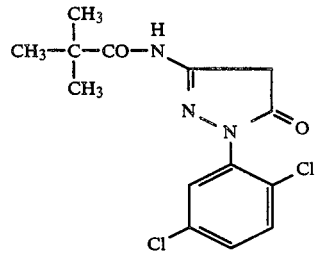

Py-9

Thioether compounds obtainable by the process according to the invention are described, for example, in DE-A-32 41 886, DE-A-36 22 007, DE-A-36 24 103 and DE-A-36 25 616. The compounds obtainable by the process according to the invention are suitable, for example, as 2-equivalent magenta couplers for colour photographic recording materials.

Although the process according to the invention has been described above with reference to 5-pyrazolone compounds, it is equally suitable for the preparation of thioether compounds which, instead of containing the group Py, contain a corresponding residue of a magenta coupler derived from imidazolo[1,2-b]pyrazole, imidazolo[3,4-b]-pyrazole, pyrazolo[2,3-b]-pyrazole, pyrazolo[3,2-c]-1,2,4-triazole, pyrazolo[2,3,-b]-1,2,4-triazole, pyrazolo[2,3,-c]-1,2,3-triazole or pyrazolo[2,3,-d]-tetrazole. Examples of such 4-equivalent magenta couplers from which the corresponding thioether compounds (2-equivalent couplers) may be prepared by the process according to the invention are shown below.

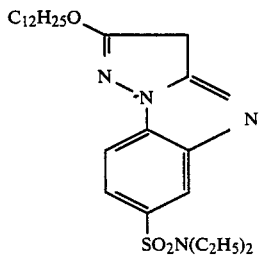

Py-10

-continued

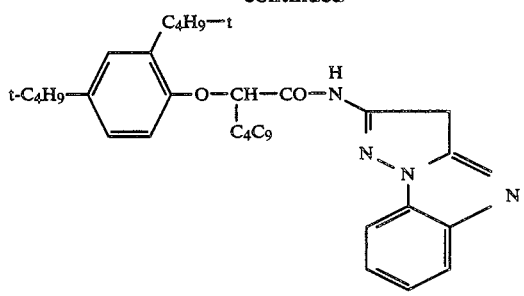
Py-11

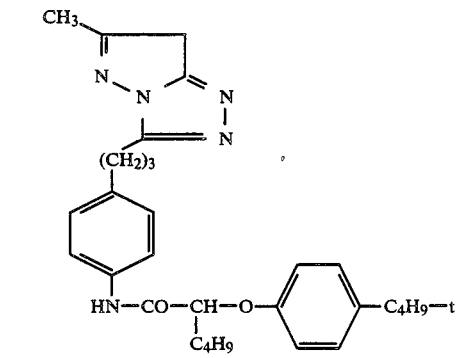
Py-12

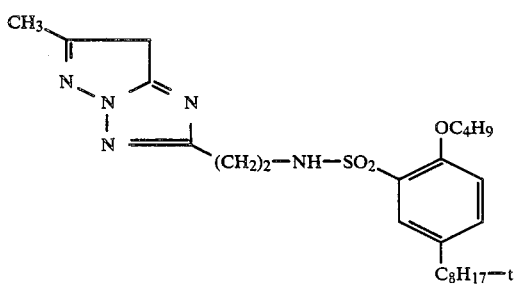
Py-13

EXAMPLE 1

Preparation of a 2-equivalent magenta coupler corresponding to formula A

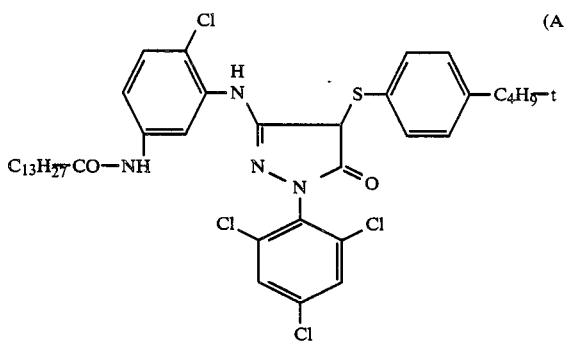
(A)

4-tert-butyl-sulphenic acid morpholide was prepared as follows:

9.9 g of 4-tert-butylthiophenol were dissolved in 80 ml of methylene chloride. 5.1 ml of sulphuryl chloride were added dropwise at 10° C. and the reaction mixture was then stirred for 30 minutes and finally concentrated by evaporation.

12.5 g of morpholine (amine component B-4) were dissolved in 50 ml of dimethylformamide. The crude sulphenic acid chloride prepared as described above was added dropwise at 10° C. and the mixture was then stirred for a further 30 minutes.

30.7 g of 1-(2,4,6-trichlorophenyl)-3-(2-chloro-5-tetradecoyl- were dissolved in dimethylformamide and the sulphenic acid amide solution was added at room temperature. 18 ml of a 30% methanolic methylate solution were then added dropwise and the mixture was stirred for 2 hours.

The reaction mixture was worked up under aqueous conditions and the crude product was separated by suction filtration and redissolved from ethanol.

Yield: 30.7 g (=79%).

m.pt. 153°–155° C.

EXAMPLES 2 TO 9

The reaction to form the same compound A was carried out by methods analogous to that described in Example 1 but sulphenic acid amide compounds containing the following amine components were used instead of the sulphonamide compound prepared from morpholine:

| Example | Amine component | Yield % |
|---|---|---|
| 2 | B-1 | 83 |
| 3 | B-5 | 85 |
| 4 | B-7 | 81 |
| 5 | B-15 | 72 |
| 6 | B-16 | 78 |
| 7 | B-19 | 69 |
| 8 | B-13 | 82 |
| 9 | B-22 | 76 |

EXAMPLE 10

(not acccording to the invention)

Preparation of compound A according to U.S. Pat. No. 3,227,554

9.9 g of tertiary butylthiophenol were chlorinated with 5.1 ml of sulphurylchloride in 80 ml of carbon tetrachloride. The solvent and HCl and $SO_2$ were evaporated off under vacuum. The highly viscous oil obtained was slowly added dropwise at 5 to 10° C. to a solution of 30.7 g of 1-trichlorophenyl-3-(2-chloro-5-tetradecanoylamidoanilino)-pyrazolone-5(Py-1) in 250 ml of carbon tetrachloride. The reaction mixture was stirred for a further 3 hours at room temperature and then heated under reflux for 30 minutes. This layer chromatography and working up of an equimolar part of the reaction mixture resulted in approximately 50% formation of the product of synthesis A.

Further graded additions of sulphenic acid chloride resulted in an approximately 2.7 times molar quantity of tertiary butyl thiophenol compared with the quantity of 4-equivalent coupler, which is the proportion of tertiary butyl thiophenyl necessary for complete conversion of the 4-equivalent coupler, albeit with considerable formation of by-products.

With this approximately 170% excess of thiophenol, the yield of compound A was 48%.

EXAMPLE 11

(not according to the invention)

Preparation of compound A (according to Research Disclosure 13 806).

Compound A was obtained in 53% yield (m.pt. 151°–152° C.) from the 4-equivalent pyrazolone Py-1 and 2.5 times molar quantity of tertiary butylthiophenol and an equally large molar quantity of bromine.

EXAMPLE 12

(not according to the invention)

Preparation of compound A according to DE-A-32 41 886

(a.) 36.5 g. of tertiary butylthiophenol were dissolved in 200 ml of methylene chloride and chlorinated with 17.8 ml of sulphenyl chloride at room temperature. After the acid gasses had been drawn off, this solution was added to a suspension of 39.2 g of an anhydrous sodium salt of toluene sulphenic acid in 150 ml of methylene chloride. The resulting reaction mixture was stirred for 1 hour and then stirred into water and the organic phase was separated off. The product obtained afer washing and concentration by evaporation was a viscous oil which required to be recrystallized from ethyl acetate/hexane for further reactions.

Yield: 51.5 g=74%.

(b.) 30.7 g of the 4-equivalent coupler Py-1 were stirred into 200 ml of methanol and 8 g of sodium methylate. 22.4 g of the thiosulphonic acid ester obtained under a., which is the quantity required for complete reaction, were added at room temperature.

Yield: 28 g=72%.

EXAMPLE 13

Synthesis of

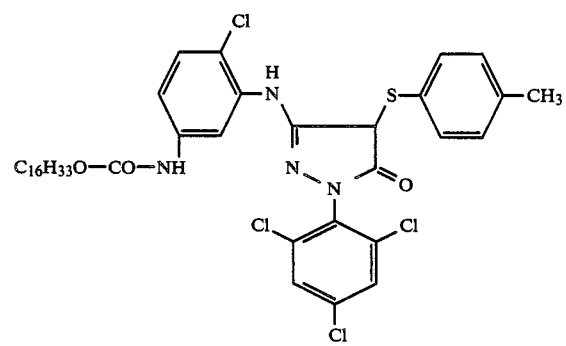

19.2 g of bromine in 50 ml of dichloromethane were added to 24.6 g of bis-[4-methylphenyl]-disulphane and 20 g of morpholine in 250 ml of dichloromethane at 10° to 15° C. in the course of 30 minutes. The reaction mixture was left to adjust to room temperature and then stirred for 2 hours and concentrated by evaporation. The oily residue left behind was added to a solution of 53.6 g of 1-trichlorophenyl-3-(2-chloro-5-cetyloxy-carbonylamino-anilino)pyrazolone-5(Py-2) in 320 ml of methanol. The reaction mixture was thereafter heated to 40° C. and 5 g of sodium methylate dissolved in 20 ml of methanol were slowly added. The reaction was completed after 30 minutes. Working up by the usual methods resulted in a yield of 46.5 g (73%) of the mixed compound.

EXAMPLE 14

Synthesis of

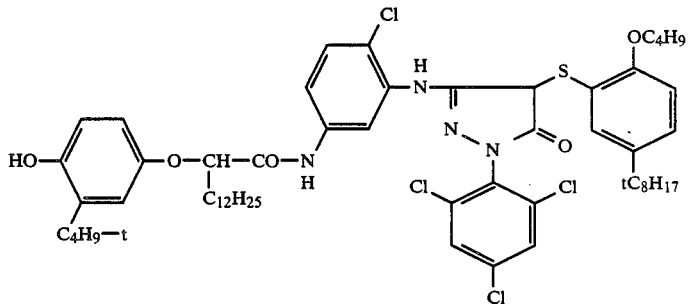

(a.) 29.3 g of 2-butoxy-5-tertiary-octylthiophenol and 14.7 g of phthalic acid imide were dissolved in 100 ml of dimethylformamide and 20 ml of triethylamine and 6.0 ml of bromine were added to the solution at 0° to 5° C. The reaction mixture was then stirred for 1 hour, poured on water, taken up with methylene chloride and separated and the organic phase was washed and concentrated by evaporation. The oil remaining behind could be crystallized from acetonitrile or used for the subsequent reaction without further purification.

Yield: 38.5 g (88%).

(b.) 39 g of 1-(2,4,6-trichlorophenyl)-3-{5-[α-(3-tertiary-butyl-4-hydroxyphenoxy)tetradecanoylamido]-2-chloroanilino}-pyrazolone-5 were dissolved in 140 ml of dimethylformamide, and a solution in 30 ml of dimethylformamide of 26.4 g of the sulphenic acid thalimide obtained as described above was added at room temperature. After 30 minutes, the reaction mixture was briefly heated to 40° C. and 60 g of sodium methylate were added. After a further 30 minutes, the reaction mixture was cooled and worked up in the usual manner. Recrystallization from ethanol.

Yield: 39.6 g (74%).

m.pt. 146°-148° C.

We claim:

1. A process for the preparation of a thioether compound of the formula Py—S—R (I), wherein:
    Py represents the residue of a 5-pyrazolone compound to which the group —S—R is attached in the 4-position, and
    R represents alkyl with up to 20 carbon atoms, cycloalkyl,
    benzyl, phenethyl
    or a heterocyclic group by the reaction of a compound of the formula Py*—H
    wherein Py* represents the residue of a 5-pyrazolone compound which is not substituted in the 4-position and from which a hydrogen atom has been removed in the 4-position
    with a reactant for the introduction of a thioether group in the 4-position of the 5-pyrazolone compound, wherein the improvement comprises the compound of the formula Py*—H is reacted with a compound of the formula B—S—R (II) wherein R has the meaning already indicated and B represents

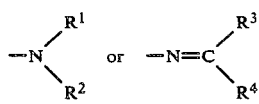

wherein $R^1$ represents alkyl, aralkyl or aryl, $R^2$ represents alkyl, aralkyl or $SO_2$—$R^5$ or $R^1$ and $R^2$ together form the residue for completing a 5-membered or 6-membered heterocyclic ring, $R^3$ and $R^4$ represents dialkylamino and $R^5$ represents alkyl, aryl or dialkylamino.

2. Process as claimed in claim 1, wherein the pyrazolone compound which is unsubstituted in the 4-position is reacted in a protic or aprotic organic solvent with one to two times the molar quantity of a compound of the formula B—S—R, wherein B and R have the meanings indicated in claim 1.

3. Process as claimed in claim 2, wherein the reaction is carried out at a temperature from 10° to 80° C.

4. Process as claimed in claim 2, wherein the compound of formula B—S—R has been produced from the corresponding disulphane (R—S—S—R) by a reaction with halogen in the presence of a secondary amine and is reacted, without further purification, with the pyrazolone compound which is unsubstituted in the 4-position.

5. Process as claimed in claims 1, 2, 3 or 4 wherein the compound Py*—H corresponds to the formula

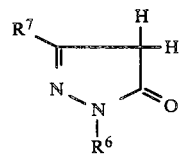

wherein $R^6$ represents an aryl group and $R^7$ denotes an amino or acylamino group.

6. Process as claimed in claim 1, wherein R represents a phenyl group which is substituted with up to three members selected from the group consisting of halogen, alkyl benzyl, alkoxy, alkylthio, carbon amido, phenoxy and nitro.

* * * * *